US012303282B2

(12) United States Patent
Kele et al.

(10) Patent No.: US 12,303,282 B2
(45) Date of Patent: *May 20, 2025

(54) FLEXIBLE ELECTROENCEPHALOGRAPHY HEADSET

(71) Applicant: Zeto, Inc., Santa Clara, CA (US)

(72) Inventors: Peter Kele, Szeged (HU); Janos Kokavecz, Szeged (HU); Gabor Braun, Salgotarjan (HU); Aswin Gunasekar, San Jose, CA (US)

(73) Assignee: Zeto, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/530,523

(22) Filed: Dec. 6, 2023

(65) Prior Publication Data

US 2024/0099644 A1   Mar. 28, 2024

Related U.S. Application Data

(63) Continuation of application No. 18/220,483, filed on Jul. 11, 2023, now Pat. No. 12,171,566, which is a (Continued)

(51) Int. Cl.
*A61B 5/291* (2021.01)
*A61B 5/00* (2006.01)
(Continued)

(52) U.S. Cl.
CPC .............. *A61B 5/386* (2021.01); *A61B 5/273* (2021.01); *A61B 5/291* (2021.01); *A61B 5/6803* (2013.01); *A61B 5/6814* (2013.01)

(58) Field of Classification Search
CPC ......... A61B 5/386; A61B 5/291; A61B 5/273; A61B 5/6803; A61B 5/6814; A61B 5/369
See application file for complete search history.

(56) References Cited

U.S. PATENT DOCUMENTS

| | | | |
|---|---|---|---|
| 2011/0015503 A1* | 1/2011 | Joffe | A61B 5/30 600/383 |
| 2011/0301486 A1* | 12/2011 | Van Hek | A61B 5/31 600/544 |

(Continued)

FOREIGN PATENT DOCUMENTS

WO   WO-2022251696 A1 * 12/2022 .............. A61B 5/16

*Primary Examiner* — Adam Z Minchella
(74) *Attorney, Agent, or Firm* — Run8 Patent Group, LLC; Peter Miller

(57) ABSTRACT

One variation of a system for locating electrodes on a head of a user includes a headset defining a set of electrode bodies elastically interconnected by a unique set of spring elements configured to locate the set of electrode bodies at electrode positions of the international 10-20 standard, irrespective of the size of the head of the user. The spring elements are configured to carry electrical signals between interconnected electrode bodies and ultimately to a controller. An electrode tip is mechanically and electrically coupled to each electrode body. The electrode tip comprises a thin conductive probe mounted at the distal end of an elastic beam and is configured to extend from a base of the electrode tip, bypass hair, and electrically couple to the head of the user, and an insulative boss, configured to rest on and transfer the weight of the headset to the head of the user.

13 Claims, 3 Drawing Sheets

Related U.S. Application Data continuation of application No. 17/882,474, filed on Aug. 5, 2022, now Pat. No. 11,744,504.

(60) Provisional application No. 63/256,238, filed on Oct. 15, 2021, provisional application No. 63/229,871, filed on Aug. 5, 2021.

(51) Int. Cl.
*A61B 5/273* (2021.01)
*A61B 5/386* (2021.01)

(56) References Cited

U.S. PATENT DOCUMENTS

| | | | |
|---|---|---|---|
| 2013/0079609 A1* | 3/2013 | Besko | A61B 5/14552 |
| | | | 600/324 |
| 2013/0085363 A1* | 4/2013 | Wada | A61B 5/6843 |
| | | | 600/383 |
| 2016/0239084 A1* | 8/2016 | Connor | A61B 5/6803 |
| 2017/0135640 A1* | 5/2017 | Gunasekar | A61B 5/6843 |
| 2017/0281036 A1* | 10/2017 | Parvizi | A61B 5/325 |
| 2018/0239430 A1* | 8/2018 | Tadi | H01L 33/58 |
| 2022/0039721 A1* | 2/2022 | Abercrombie | A61B 5/02438 |

\* cited by examiner

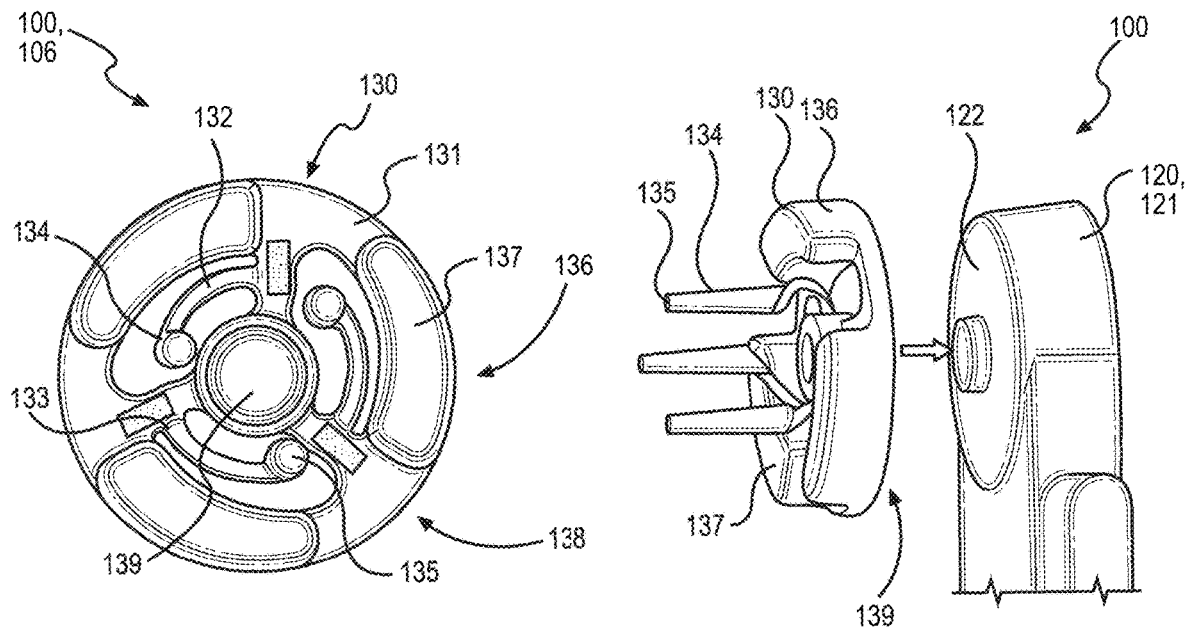
FIGURE 2A
FIGURE 2B
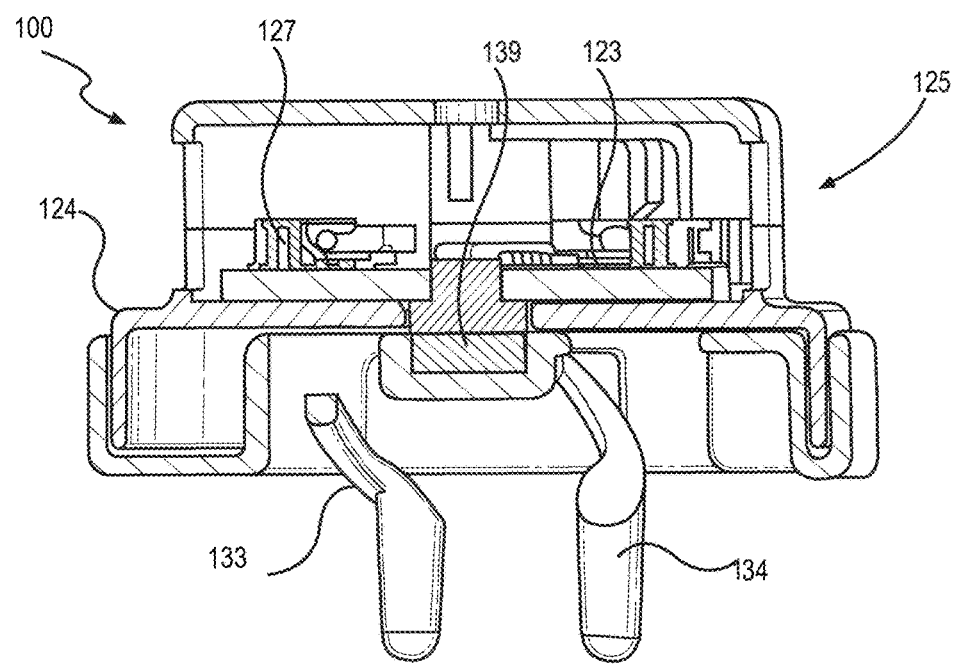
FIGURE 2C

FLEXIBLE ELECTROENCEPHALOGRAPHY HEADSET

CROSS-REFERENCE TO RELATED APPLICATIONS

This application is a continuation of U.S. patent application Ser. No. 18/220,483, filed on 11 Jul. 2023, which is a continuation of U.S. patent application Ser. No. 17/882,474, filed on 5 Aug. 2022, which claims the benefit of U.S. Provisional Application No. 63/229,871, filed on 5 Aug. 2021, and U.S. Provisional Application No. 63/256,238, filed on 15 Oct. 2021, each of which are incorporated in its entirety by this reference.

This application is related to U.S. patent application Ser. No. 15/351,016, filed on 14 Nov. 2016, which is incorporated in its entirety by this reference.

TECHNICAL FIELD

This invention relates generally to the field of electro-encephalopathy and more specifically to a new and useful method for collecting electrical measurements in the field of electro-encephalopathy.

BRIEF DESCRIPTION OF THE FIGURES

FIGS. 2A-2C are schematic diagrams of one variation of the system; and

DESCRIPTION OF THE EMBODIMENTS

Figure 1:
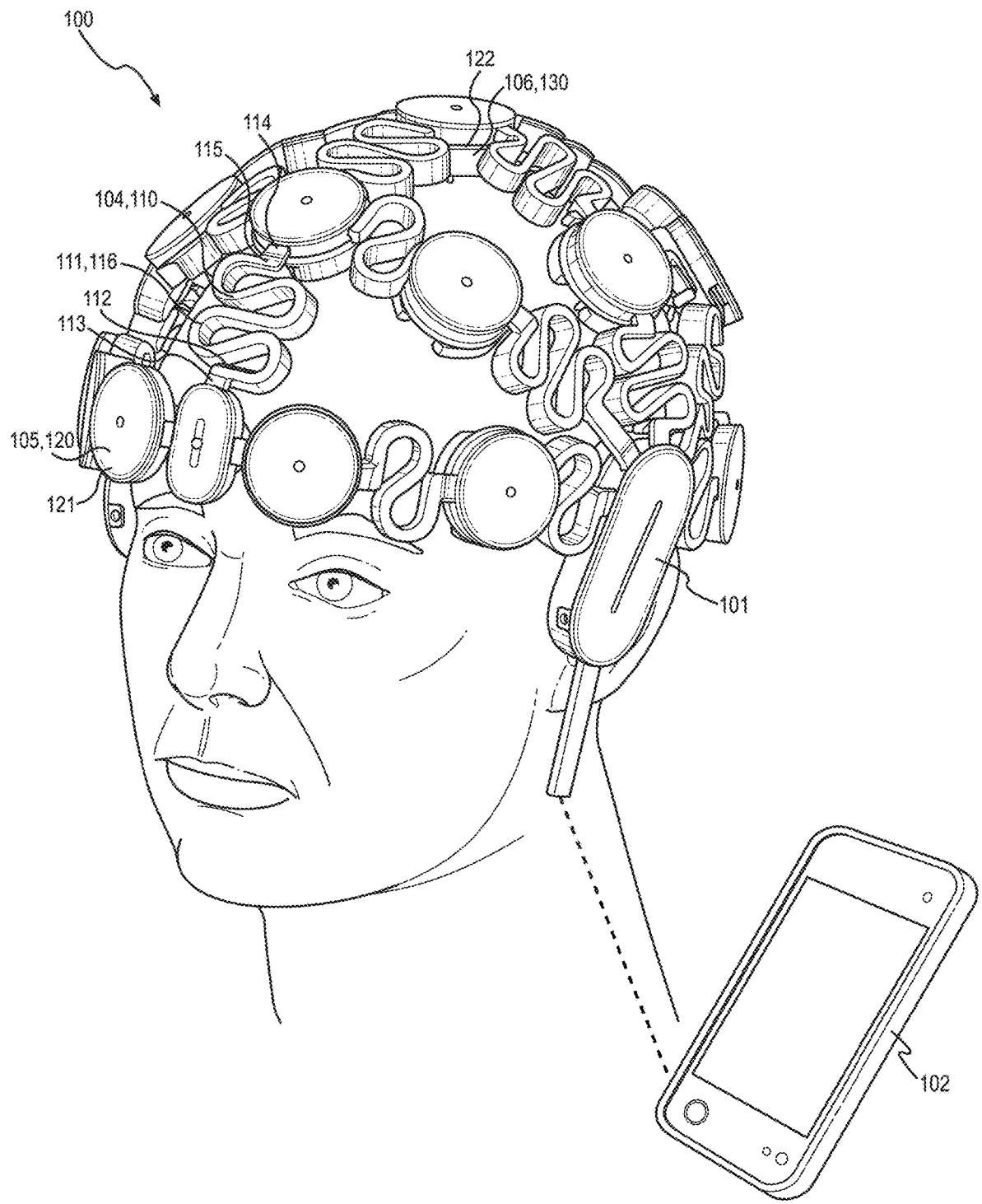
FIG. 1 is a schematic diagram of a system.

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. System

Generally, a system 100 for locating electrodes on a head of a user includes a set of electrode bodies configured to locate at electrode positions of an electroencephalography (or "EEG") standard, such as the international 10-20 system, forming an EEG headset. In one implementation, the system 100 can include an electrode body defining an electrode body 120 that can include a base, a cavity, an annulus, an electrode tip 130, a conductive element (e.g., a flexible PCB), an electrode interface 122, a spring element receiver 126, and an electrical circuit 123 (e.g., a local signal circuit). The conductive element can be electrically coupled to and configured to transmit data between the electrical circuit and a controller 102. The housing is also configured to retain (or "lock") a set of spring elements 104 within spring element receivers 126 of the base. The system includes a set of spring elements 104 configured to: mechanically couple adjacent electrode bodies 120; to expand and contract to accommodate different head sizes and shapes; and to locate adjacent electrodes 120 in relative positions that approximate an EEG standard (e.g., the 10-20 system). The system can include a controller 102 configured to receive electrical signals from the set of electrode bodies 105, process the electrical signals to produce an output, and transmit the output to an output device (e.g., a monitor or a computer) to further process, analyze, or display the output to a user or operator.

In another implementation, as shown in FIGS. 1-3B, the system 100 includes a headset 101 defining a set of electrode bodies 105 configured to detect electroencephalographic signals from the head of the user; and a set of spring elements 104 elastically interconnecting a set of electrode bodies 105 and configured to locate the set of electrode bodies 105 on the head of the user. Each spring element 110 in the set of spring elements 104 can include a spine 111 defining: a proximal end 112 including a first arcuate section 113 extending about a first axis, configured to elastically deform about the first axis to accommodate a curvature of the head of the user, and configured to electrically couple to a first electrical circuit 123 within a first electrode body 120 in the set of electrode bodies 105; a distal end 114 including a second arcuate section 115 extending about a second axis, configured to elastically deform about the second axis to accommodate the curvature of the head of the user, and a second electrical connector configured to electrically couple to a second electrical circuit 123 within a second electrode body 120 in the set of electrode bodies 105; and a center section 116 defining a serpentine geometry extending between the proximal end 112 and the distal end 114, and configured to elastically deform between the first axis and the second axis to accommodate a size of the head of the user. Each spring element no in the set of spring elements 104 further includes a conductive element 117, extending between the proximal end 112 and the distal end 114, along the center section 116, and configured to conduct electrical signals between the first electrode body 120 and a second electrode body 120.

In yet another implementation, as shown in FIGS. 1-3B, the system 100 includes a headset 101 defining a set of electrode bodies 105 and a set of spring elements 104. Each electrode body 120 in the set of electrode bodies 105 includes: a housing 121 defining an electrode interface 122 configured to receive an electrode tip 130; and an electrical circuit 123 arranged within the housing 121 and electrically coupled to the electrode interface 122. Each spring element 110 in the set of spring elements 104 defines a serpentine geometry extending between a first electrode body 120 and a second electrode body 120 in the set of electrode bodies 105 and is configured to: elastically deform between the first electrode body 120 and the second electrode body 120; and communicate electrical signals between a first electrical circuit 123 in the first electrode body 120 and a second electrical circuit 123 in the second electrode body 120. The system 100 further includes a set of electrode tips 106, each electrode tip 130 in the set of electrode tips 106 defining: an electrode base 131 defining a conductive material, configured to transiently install on the housing 121, and configured to electrically couple to the electrode interface 122; an elastic beam 132 including the conductive material and extending from the electrode base 131; a conductive probe 134 arranged on a distal end of the elastic beam 132 opposite the electrode base 131, defining a first contact area 135 configured to contact and electrically couple to the head of the user, and configured to conduct electrical signals from the head of the user to the electrode interface 122 via the elastic beam 132 and the electrode base 131; and a boss 136 including an insulative material, extending from the electrode base 131 opposite the electrode interface 122, and defining a second contact area 137 greater than the first contact area 135, configured to contact the head of the user, and to transfer a weight of the headset 101 to the head of the user.

2. Applications

Generally, the system includes a set of unique components (i.e., springs and electrodes) assemblable into a headset (e.g., an EEG headset) configured to locate a constellation of electrode bodies 106 according to an EEG standard (e.g., the 10-20 system) for a population of users exhibiting different head shapes and sizes. In particular, the system includes a set of spring elements 104 interposed between and configured to connect a set of electrode bodies 105. The set of spring elements 104 exhibit different characteristic springs rates and are distributed across the headset 101 to absorb different head sizes.

Generally, the headset 101 includes a set of electrodes constructed from minimal parts. Electrode bodies and spring elements can be formed from an injection molded polymer. The headset 101 can be quickly assemblable and configurable by an operator with limited skill. Spring elements can attach to electrodes via interference fit. When assembled, the headset 101 requires minimal adjustment to locate electrodes according to an EEG standard. Therefore, the headset 101 can be quickly deployed to record an accurate EEG result with limited operator skill. The spring element no can be arranged in a serpentine shape to construct a flat spring and can include a hollow channel. The hollow channel can contain a cable within the spring element 110 connecting adjacent electrodes. The spring element 110 can be arranged such that adjacent and nominally-parallel sections of the spring element 110 are offset, and each return end of a spring element 110 maintains a gap between the adjacent section and the return end to reduce or eliminate pinch points that may catch or pull on a user's hair while wearing the headset 101. The flat spring can rest against the user's head and distribute the weight of the headset such that the entire weight of the headset is not carried solely by the contact of the electrode tip 130s against the user's scalp. Further, due to minimal weight and number of parts, the headset imparts minimal pressure to a user's head via the electrode tip 130s and spring elements, allowing the user to wear the headset for an extended period of time with minimal discomfort. Additionally, the minimal construction of the headset allows a user to freely assume a variety of positions (e.g., sitting, standing, or lying down) or move their head while wearing the headset 101. Components providing functions such as processing and power can be located in a controller 102 external from the headset.

2.1 Spring Element Longitudinal Extension and Angular Flexion

Each spring element 110 in the set of spring elements 104 is configured to elastically deform along a longitudinal axis according to a spring rate to conform to the size of a user's head when locating the set of electrode bodies 105. The spring rate of each spring element 110 in the set of spring elements 104 is tuned such that extension of each of the spring elements 110 results in a controlled ratio of expansion between adjacent electrode bodies 120, which corresponds to positions of electrodes as defined by an EEG standard (e.g., international 10-20 standard). Each spring element 110 interconnects two adjacent electrode bodies 120 and exhibits a spring rate matched to the expansion ratio between the two adjacent electrode bodies 120 according to the EEG standard. Generally, spring elements 110 are configured to exhibit different spring rates based on the number of loops (or turns) of the serpentine geometry. Additionally a spring element no can be configured to exhibit a spring rated based on the cross-sectional area of the spring element 110, and/or the elasticity of the material of the spring element 110. The set of spring elements 104 includes multiple spring elements no exhibiting multiple spring rates, and each spring element no in the set of spring elements 104 is configured to cooperate with other spring elements 110 in the set of spring elements 104 to locate the set of electrode bodies 105 according to an EEG standard for a range of head sizes without reconfiguration (e.g., without changing or replacing spring elements 110.)

Spring elements no can additionally include a set of arcuate sections configured to elastically deform along an angular direction to conform to the curvature of a user's head. Additionally, the spring elements no can elastically deform through a range of angles to accommodate a range of curvatures (e.g., multiple curvatures of multiple heads, multiple local curvatures of a single head). The set of arcuate sections can include a proximal arcuate section 113 and a distal arcuate section 115 located at opposite ends of a center section 116 of the spring element no defining the serpentine geometry. Spring elements no can elastically deform along the angular direction independent of the longitudinal axis, and vice-versa, thereby decoupling the longitudinal movement enabled by the longitudinal elastic deformation of the serpentine geometry and angular movement enabled by the angular elastic deformation of the proximal arcuate end 113, the distal arcuate end 115, or both. Therefore spring elements no can conform individually to the size and/or curvature of a user's head.

Each spring element no includes a spine 111 exhibiting the spring rate of the spring element no (longitudinal and angular) extending from a proximal end 112 to a distal end 114, and a conductive element 117 defining a flexible PCB mounted to the spine 111. The conductive element 117 extends between a proximal end 112 and a distal end 114 of the spine 111 and extends from the proximal end 112 to form a proximal electrical connector and extends from the distal end 114 to form a distal electrical connector. The conductive element 117 is configured to conduct electrical signals between the proximal electrical connector and the distal electrical connector while elastically deforming according to the elastic deformation of the spine 111. Spring elements 11o including an odd number of turns of the serpentine geometry can include the conductive element 117 mounted to one side of the spine 111 of the spring element 110 to position the proximal electrical connector in an orientation to interface with the electrical receiver of a first housing 121 and position the distal electrical connector in an orientation to interface with the electrical receiver of a second housing 121. Spring elements no, including an even number of turns of the serpentine geometry, can include the conductive element 117 mounted to a first side of the spine 111 and a second side of the spine 111 and include a transition from the first side to the second side. The conductive element 117 is mounted to the first face of the spine 111 to position the proximal electrical connector in an orientation to interface with the electrical receiver of a first housing and the conductive element 117 is mounted to the second face of the spine 111 to position the distal electrical connector in an orientation to interface with the electrical receiver of a second housing. Additionally, each spring element no is covered (e.g., dip molded, over molded, spray coated, cast) with an insulative and/or protective material to insulate and/or protect the spine 111 and conductive element 117.

2.2 Distribution of Headset Weight Via Electrode Tips

The electrode tip 130 includes an elastic beam 132, a conductive probe 134 cantilevered on a distal end of the elastic beam 132, and a boss 136. The conductive probe 134 defines a first contact area 135, configured to contact and electrically couple to the scalp of the user. The boss 136 defines a second contact area 137, greater than the first contact area 135. The electrode tip 130 is configured to rest against the head of the user either on the hair, on the skin of the head, (such as on the forehead) or directly on the scalp (in the case of a bald user) and carry a local portion of the weight of the headset 101 to the head of the user via the boss 136. The conductive probe 134 is arranged cantilevered on the distal end of an elastic beam 132 exhibiting a spring rate. The elastic beam 132 is configured to drive the conductive probe 134 toward the head of the user in a resting position. The boss 136 resting on the head of the user decouples the local weight of the headset 101 from the force of the elastic beam 132, driving the conductive probe 134 toward the head of the user, thereby limiting the force exerted by the first contact area 135 of the conductive probe 134 on the head of the user to the force exerted by the elastic beam 132 corresponding to the spring rate of the elastic beam 132.

In one example in which the user has hair, the conductive probe 134 passes between individual hairs of the user and contacts the scalp of the user beneath the hair. The force of the elastic beam 132 is sufficient to maintain the conductive probe 134 in contact with the head of the user, thereby maintaining an electrical coupling between the conductive probe 134 and the head of the user. The weight of the headset 101 is carried to the head of the user via the larger second contact area 137 of the boss 136, and only the force exerted by the elastic beam 132 is applied to the conductive probe 134 and, thereby to the user.

In another example, the electrode tip 130 is positioned on a region of the head of the user devoid of hair (e.g., the forehead, a bald scalp) and includes a recess 108 arranged between a first boss 136 and a second boss 136. The elastic beam 132 is configured to guide the conductive probe 134 into the recess 138 in response to the scalp of the user in contact with the second contact area 137 of the first boss 136. The local weight of the headset 101 is carried to the head of the user via the second contact area 137 of the first boss 136 (and the second contact area 137 of the second boss 136) and decoupled from the force exerted by the elastic beam 132 on the conductive probe 134 for a location on the head of a user devoid of hair.

Therefore, the headset 101 equipped with a single electrode tip configuration can be applied to several users with heads of different hair and scalp attributes, without customizing the headset 101 or interchanging electrode tips 130 for each user, thereby reducing the number of headset configurations and electrode tip configurations necessary to electrically couple an electrode tip 130 effectively to the head of a user.

In another implementation, the system 100 includes an electrode tip 130 defining a unitary structure including a conductive probe 134 formed from a conductive polymer, and a boss 136 formed from an insulative polymer. The electrode tip can be formed as a single injection molded polymer part including a first injection of the conductive polymer and a second injection of the insulative polymer, the insulative polymer bonding to the conductive polymer during the injection molding process. The insulative polymer can be selectively bonded to the conductive polymer to limit the exposed area of conductive polymer to electrical contact surfaces (such as electrode contact surfaces or an electrical interface between an electrode tip and an electrode housing.) Further, the conductive polymer can be integrated within the electrode housing to form an electromagnetic shield 124, isolating the local contact area of an electrode tip from external electromagnetic interference, thereby increasing the clarity of an EEG signal. The electrode tip 130 can be configured to transiently install in an electrode housing via magnetic attachment allowing a rotational degree of freedom and enabling fine tuning of the placement of the conductive probe on the head of the user. In one variation, the headset 101 includes a set of mass produced, single-use sanitary electrode tips 130 that can be discarded after an EEG of each user.

3. Electrode Bodies

As shown in FIG. 1, the EEG headset includes a set of electrode bodies 105 configured to locate at points of an EEG standard, such as the international 10-20 system. The set of electrode bodies can divide into subsets. A first subset of (e.g., two) electrode bodies can arrange five spring receivers (e.g., at 0°, 45°, 90°, 135°, and 180° positions) and a strap connector (e.g., at 270° position) and can be configured to locate at T3 and T4 locations. A second subset of (e.g., three) electrode bodies can include four spring receivers (e.g., at 0°, 90°, 180°, and 270° positions) and can be configured to locate at Fz, Cz, and Pz locations. A third subset of (e.g., two) electrode bodies an include three spring receivers (e.g., at 0°, 90°, and 180° positions) and can be configured to locate at FpZ and Oz locations. A fourth subset of (e.g., fourteen) electrode bodies can include two spring receivers (e.g., at 0° and 180°. positions) and can be configured to locate at Fp1, F7, T5, O1, O2, T6, F8, Fp2, F3, F4, C3, C4, P3, P4, locations.

In one implementation, an electrode body 120 can include a base with a castellated perimeter wall encircling a cavity and defining a set of spring receivers, and an annulus facing downwardly from the cavity opposite the spring receivers and configured to receive an electrode tip 130. An electrical circuit 123 can be arranged in the cavity over the annulus. An electrode interface 122 can be arranged on the housing 121 and is configured to electrically couple to an electrode tip 130. The electrical circuit 123 (e.g., a local signal circuit, an amplifier circuit) can be arranged within the housing 121 and configured to read and condition an EEG signal from the electrode tip 130. A connector can be arranged on the electrical circuit 123 and configured to transmit data received from the electrical circuit 123 to a controller 102, and to receive power input. A cover can be arranged over the base over the cavity and configured to enclose the electrical circuit 123 within the cavity and retain (or "lock") a set of springs within the spring receivers of the base. For example, the cover can interface with the castellated perimeter wall of the base to construct a spring receiver, and a spring element 110 can insert into the spring receiver in an interference (or "snap") fit. An annular cushion can be arranged on the base about the annulus and opposite the cover and configured to carry weight of the electrode to a scalp. For example, the annular cushion can be an elastic material (e.g., silicone, memory foam) and can be bonded the base about the annulus. In one variation, the system includes a kit of the annular cushions that are interchangeable to suit different electrode sizes. An electromagnetic shield 124 can be arranged within the housing 121 between the electrical circuit 123 and the cover and configured to shield an electrode tip 130 installed on the electrode interface 122 from ambient electrical noise.

In one implementation, the electrode body is formed from a conductive polymer and an insulative polymer as a unitary structure. The electrode body can include the housing 121 enclosing the electrical circuit 123, formed from the insulative polymer, and the electrode interface configured to receive and electrically couple to an electrode tip 130 formed from the conductive polymer. Additionally, the housing 121 can include conductive polymer arranged to form an electromagnetic shield 124 configured to shield the electrode tip 130, and the local area of the head of the user to which the electrode tip 130 is electrically coupled, from external electromagnetic radiation.

For example, as shown in FIG. 2C, the electrode body 120 defines a unitary structure and includes a housing 121 formed from an insulative polymer; an electrode interface 122 formed from a conductive polymer; and an electromagnetic shield 124 formed from a conductive polymer, extending from the electrode interface 122 toward the head of the user, radially offset from and encircling the boss 136, and configured to shield the conductive probe 134 from external electromagnetic radiation.

Therefore, the electromagnetic shield 124 can reduce extraneous electromagnetic noise by shielding the electrode tip 130 and the local area of the head of the user to which the electrode tip 130 is electrically coupled, thereby resulting in a higher quality signal from the electrode tip 130. In particular, the electromagnetic shield can reduce undesirable artefacts in the EEG such as electrical mains artifacts or capacitive coupling artifacts (e.g., sudden movements, waving hands around the user).

In another implementation, the electrical circuit 123 includes a light element (e.g., a multi-color LED, a light ring) arranged on the housing 121. A controller 102 (described below) can implement methods and techniques described in application number U.S. Ser. No. 15/351,016 which is incorporated by reference, to: track contact quality between an electrode tip 130—installed in the electrode body 120—and a user's scalp; set the light element to a first color (e.g., green) if contact quality of the electrode tip 130 exceeds a threshold contact quality; set the light element to a second color (e.g., yellow) if contact quality of the electrode tip 130 is varying at greater than a threshold frequency; and/or set the light element to a third color (e.g., red) if contact quality of the electrode tip 130 is less than the threshold contact quality.

3.1 Electrode Tip

Generally, an electrode tip 130 cooperates with an electrode body 120 and an electrical circuit 123 arranged within the electrode body 120 to define an "electrode." The electrode is configured to contact the skin of a user, to detect local neural oscillations on the user's skin, and to transmit data representing these local neural oscillations to the controller 102. For example, the electrode can detect a high-impedance sense signal from the user's skin; convert this high-impedance sense signal into a low-impedance sense signal; and pass this low-impedance sense signal to the controller 102 via a wired connection passing through one or a series of spring elements between the electrode and the controller 102. The electrode can be formed from a conductive material (i.e., metal, non-metallic, conductive foam, conductive polymer). The system can include a kit of electrode tips 130 that are electrically conductive, configured to transiently install in the set of electrode bodies 105, and defining a set of configurations such as: flat or domed (e.g., for no hair), short bristles (e.g., for short, thin, and/or straight hair), or long bristles (e.g., for long, voluminous, curly hair).

In one implementation as shown in FIGS. 2A-2C, the electrode tip 130 includes a conductive probe 134 mounted to the distal end of an elastic beam 132 configured to extend the conductive probe 134 from the electrode base 131 toward the surface of the head of the user. The conductive probe 134 is formed from a conductive material (e.g., a conductive polymer) and defines a first contact area 135 at the tip of the conductive probe 134. The conductive probe 134 defines a small cross-section relative to the length of the conductive probe, (e.g., a needle-like structure) to pass through the hair of a user and contact the skin of the user's scalp via the first contact area 135. The electrode tip 130 further includes a boss 136 formed from an insulative material (e.g., an insulating polymer) extending from the electrode base 131, defining a larger cross-section relative to the length of the extension of the boss 136 from the electrode base, and defining a second contact area 137 larger than the first contact area 135. The electrode tip 130 further includes a recess 138, proximal the boss 136, into which the conductive probe 134 retracts when under a load produced by contact with the head of a user.

For example as shown in FIGS. 2A-2C, the electrode tip 130 includes an elastic beam 132 coupled to the electrode base 131 via a flexion joint 133 configured to: extend the conductive probe 134 toward the surface of the head in an unloaded state; and retract the first contact area 135 of the conductive probe 134 into a recess 138 adjacent the boss 136 in a loaded state.

In another example, the system 100 includes an electrode tip 130 further including a central electrode tip: extending from the electrode base; defining a third contact area configured to contact and electrically couple to the head of the user; including the conductive polymer exposed at the third contact area and extending to and electrically coupling to the electrode base; including the insulative polymer bonded to and encasing the conductive polymer between the third contact area and the electrode base; and configured to contact and conduct electrical signals from the head of the user to the first electrode interface via the first electrode base.

In another example, the system 100 includes an electrode tip 130 including: an elastic beam 132 mounted to an electrode base 131 at a proximal end and including the conductive polymer; a conductive probe 134 mounted to the elastic beam 132 at a distal end, including the conductive polymer extending from a first contact area 135 to the elastic beam 132, and configured to electrically couple the first contact area 135 to the electrode base 131 via the elastic beam 132. The electrode tip 130 further includes a boss 136: separately mounted to the electrode base 131 radially offset from the conductive probe 134 and the elastic beam 132; including the insulative polymer; and extending from the electrode base 131.

In another example, the electrode tip 130 defines a unitary structure including: an electrode base including the conductive polymer, configured to transiently install on the housing, and configured to electrically couple to the electrode interface; an integrated elastic beam extending from the electrode base including the conductive polymer and the insulative polymer bonded to and encasing the conductive polymer between the electrode base and a distal end; an integrated conductive probe arranged at a distal end of the elastic beam opposite the electrode base, defining a first contact area configured to contact and electrically coupled to the head of the user, configured to conduct electrical signals from the head of the user to the electrode interface via the elastic beam and the electrode base, including the conductive polymer extending from the first contact area to the distal end, and including the insulative polymer bonded to and encasing the conductive polymer between the first contact area and the elastic beam; and an integrated boss including the insulative polymer, extending from the electrode base opposite the electrode interface, and defining a second contact area greater than the first contact area, configured to contact the head of the user, and to carry a weight of the headset to the head of the user.

In one variation, the electrode tip can include multiple conductive probes 134 cooperating to increase the surface area of the electrode tip 130 in contact with an electrically coupled to the head of a user, and multiple bosses 136 to increase to increase the surface area transferring the weight of the headset to the head of the user. The electrode tip 130 conductive probes 134 and bosses 136 arranged in a radially symmetrical pattern, with the gaps between the bosses 136 forming the recesses 138.

In one example, the electrode tip 130 additionally includes: a second elastic beam 132 arranged circumferential to the first elastic beam 132, including the conductive material and extending from the electrode base 131; and a second conductive probe arranged on a distal end of the second elastic beam opposite the first electrode base, defining a third contact area configured to contact and electrically couple to the head of the user and configured to conduct electrical signals from the head of the user to the first electrode interface via the second elastic beam and the first electrode base. The electrode tip 130 additionally includes a second boss, circumferential to the first boss: including the insulative material; extending from the first electrode base opposite the first electrode interface; and defining a fourth contact area greater than the third contact area, configured to contact the head of the user, and to carry a weight of the headset into the head of the user.

The electrode tip 130 is configured to contact the head of a user such that the boss 136 rests on the head of the user, either on the hair, on the skin of the head, (such as on the forehead) or directly on the scalp in the case of a bald user. In one example in which the user has hair, the conductive probe 134 pierces the hair of the user and contacts the scalp of the user beneath the hair. The conductive probe 134 experiences resistance as it contacts the scalp of the user. In response, the elastic beam 132 deforms under this resistance, and the conductive probe 134 retracts toward the electrode base 131 and partially into the recess 138. The force of the elastic beam 132 is sufficient to maintain the conductive probe 134 in contact with the head of the user, thereby maintaining an electrical coupling between the conductive probe 134 and the head of the user. However, the weight of the headset 101 is transferred to the head of the user via the larger second contact area 137 of the boss 136. The elastic beam 132 may not deform at all when the electrode tip 130 is positioned on the head of a user with particularly large volume of hair.

In another example in which the local area to which the electrode tip 130 is in contact does not include hair (e.g., the forehead, the head of a bald user), an electrode tip 130 includes a conductive probe 134 of a length equal to the length of the boss 136, such that under a load, the conductive probe 134 will retract entirely into the recess 138, and therefore the first contact area 135 of the conductive probe 134 and the second contact area 137 of the boss 136 will be coplanar (e.g., both resting against the scalp of the user). As the conductive probe 134 contacts the scalp of the user and experiences resistance, the elastic beam 132 deforms under this resistance in response, and the conductive probe 134 retracts toward the electrode base 131 completely into the recess 138. The second contact area 137 of the boss 136 transfers the weight of the headset to the user, while the first contact area 135 of the conductive probe 134 is held against the head of the user by the force of the elastic beam alone.

This results in a comfortable experience for the user, as the weight of the headset 101 is distributed across the larger second contact area 137, rather than entirely concentrated at the first contact area 135 of the conductive probe 134.

Therefore, a single electrode tip configuration can be applied to several user types with different hair and scalp attributes, or to a user with multiple hair patterns across their head (e.g., receding hairline, bald spot) without customizing the headset 101 or interchanging electrode tips 130 of different configurations, thereby reducing the number of electrode tip configurations necessary to electrically couple an electrode effectively to the head of a user.

3.2 Mechanical Coupling

In one implementation, the electrode interface 122 of an electrode body 120 defines a retention aperture above and centered over the annulus of the electrode body 120, and an electrical trace adjacent and/or encircling the retention aperture. In this implementation, an electrode tip 130 includes an electrode base 131 configured to seat in an annulus of an electrode body 120, a contact end arranged on a distal end of the electrode base 131 opposite the electrode body 120 and configured to contact a scalp of a user, and a barb extending rearward from the electrode base 131 and configured to insert into and retain the retention aperture of the electrode interface 122 in the electrode body 120. For example, the electrode base, the contact end, and the barb define a unitary elastic structure (e.g., an injection-molded polymer) autocatalytically coated with a conductive material (e.g., nickel). The barb can be elastic and can deform when inserted into the retention aperture and can expand behind the electrode interface 122 to retain the electrode within the aperture of the electrode body 120 and maintain mechanical contact and electrical connectivity between the electrode base 131 and the electrical trace adjacent the retention aperture. Therefore, the retention aperture of the electrode interface 122 and the barb of the electrode tip 130 can cooperate to mechanically retain the electrode tip 130 within the electrode body 120 and to maintain electrical contact between electrical trace on the electrode interface 122 and the electrode tip 130. For example, to install the electrode tip 130 in the electrode body 120, a user pushes the electrode tip 130 into the annulus of the electrode body 120 to seat the barb in the retention aperture. To replace the electrode tip 130, a user pulls the electrode tip 130 out of the electrode body 120. Furthermore, minimal parts are needed to construct the electrode. The barb is molded into the electrode base, and the retention aperture is fabricated directly into the electrode interface 122 at time of manufacture.

3.3 Magnetic Coupling

In another implementation, the electrode interface 122 of an electrode body 120 defines an electrical trace facing the annulus. The electrode body 120 further includes a magnet, such as centered on the electrode interface 122 over and opposite the annulus. The electrode tip 130 includes an electrode base 131 configured to seat in an annulus of an electrode body 120, and a magnetic element (e.g., an iron insert) arranged in the electrode base.

In one example, the electrode body 120 defines a housing including a first magnetic element arranged at the electrode interface 122; and the electrode tip 130 includes an electrode base 131 defining a second magnetic element configured to transiently couple to the first magnetic element to retain the electrode tip 130 on the housing 121 via a magnetic connection and rotate freely about an axis perpendicular to the electrode interface 122.

In another example, the electrode base, contact end, and the magnetic element can define a unitary structure autocatalytically coated with a conductive material (e.g., nickel). The magnetic element is a magnetic material (e.g., Iron or steel). Magnetic polarity is configured such that the magnetic element is magnetically attracted to the magnet within the electrode body 120. Magnetic attraction between magnet and magnetic element can function to retain the electrode within the aperture of the electrode body 120 and maintain mechanical contact and electrical connectivity between the electrode base 131 and the electrical trace adjacent the retention aperture. Therefore, the magnet and the magnetic element can cooperate to constrain the vertical position of the electrode tip 130 within the electrode body 120. The annulus and the electrode base 131 can cooperate to constrain the lateral position of the electrode tip 130 within the electrode body 120. For example, to install the electrode tip 130 in the electrode body 120, the user places the electrode tip 130 in the annulus of the electrode body 120 to magnetically couple the magnetic element in the electrode to the magnet in the electrode body 120. To replace the electrode tip 130, the user pulls the electrode tip 130 out of the electrode body 120. Furthermore, minimal parts are needed to construct the electrode. The magnetic element is permanently fixed to the electrode tip 130, and the magnet is fixed within the electrode body 120 at time of manufacture.

3.4 Electrode Tip Geometry

In one implementation, each electrode defines a dry EEG electrode including a substrate, a set of electrically conductive bristles (e.g., short bristles, long bristles or a flat or domed conductive end), and an amplifier coupled to the substrate opposite the electrically conductive bristles. In another implementation, the electrode tip 130 defines a conductive probe 134 configured to electrically couple to the head of the user and an insulative boss 136 configured to contact the head of the user and transfer a weight of the headset into the head of the user.

3.5 Photosensor Housing

In one variation of an electrode body 120, the cover defines a cover aperture. The electrical circuit 123 includes a light sensor element (e.g., photodiode, bipolar phototransistor, or photoFET) proximal the cover aperture. The light sensor element is configured to detect light signals corresponding to properties of light detected (e.g., intensity, color, frequency of pulses when using a strobe, time length of exposure, etc.), to convert these light signals into electrical signals, and to transmit these electrical signals to the controller 102 configured to track and process light stimulation data, as described below. The photosensor housing can be interchanged with an electrode body 120 or bridge housing, as described below. For example, in this variation, the headset can assemble with a photosensor housing in preparation for an EEG test specifying a strobe stimulus. Later, the headset can be reassembled without the photosensor housing, such as to reduce weight of the headset, to reduce complexity of the headset, or to replace the photosensor housing with a vibratory housing including a vibrator in preparation for an EEG test specifying a tactile stimulus.

3.6 Bridge Housing

In one variation, a housing includes elements to electrically connect to a set of spring elements 104. A bridge housing functions to connect electrode bodies 105 adjacent to the bridge housing to one another. A bridge housing can include an electrical circuit 123 configured to boost or amplify an incoming signal and transmit this boosted signal as output to the controller 102. Generally, a bridge housing 121 includes an annular cushion similar to other electrode bodies 120, and therefore can be used to reduce the electrode pressure exerted on a user's scalp by an adjacent electrode body 120 by supporting some of the weight of the adjacent electrode body 120.

3.7 External Connection Housing+Chinstrap

Generally, the external connection housing includes an external connection to a controller and power source. The headset 101 includes an external connection to transmit data and receive power. An external connection cable connects the external connection housing to the controller 102. Signals from the set of electrode bodies 105 pass through this external connection cable to the controller 102. In one implementation, the external connection and chinstrap housing are physically coextensive, and the system includes external connection and chinstrap housings at the T3 and T4 locations.

In another implementation, the external connection housing can be placed at the O1 and O2 locations, and the external connection cable or cables routed to the controller 102. However, the external connection housing may be placed in any location to maximize the quality of the electrical signals transmitted from the EEG headset based on the user's position.

In one variation, a body of an electrode body 120 configured for arrangement near a user's temple (e.g., a T3 or T4 position) further includes a strap receiver configured to selectively receive and retain a distal end of an adjustable chinstrap.

Generally, securing the headset to the user can be necessary during recording of an EEG. Due to the sensitivity required to accurately measure local neural oscillations on the skin to record an accurate EEG, it is desirable that electrode tips 130 do not move relative to their initial position on the head of the user during the EEG recording. To reduce undesirable movement of the electrode tips 130 during an EEG measurement, a securement strap (e.g., a chin strap, a flexible jaw strap, a chest strap) is secured to one or more electrode bodies 120 and secured to the user.

In one example, the system can include a T3 electrode body 120 defining a first strap receiver; a T4 electrode body 120 defining a second strap receiver; a first insert pivotably coupled to a proximal end 112 of the adjustable chinstrap and configured to insert into the first strap receiver and to fixedly couple the proximal end 112 of the adjustable chinstrap to the T3 electrode body 12o; and a second insert pivotably coupled to a distal end 114 of the adjustable chinstrap; configured to insert into the second strap receiver and to fixedly couple the distal end 114 of the adjustable chinstrap to the T4 electrode body 120.

In another example, a first electrode body 120 includes an electrode tip 130 in contact with the head of the user positioned at a first mastoid reference proximal a first ear of the user; a second electrode body 120 includes an electrode tip 130 in contact with the head of the user positioned at a second mastoid reference proximal a second ear of the user and includes an accelerometer 127; and the controller 102 is electrically coupled to the headset 101 via the second electrode body 120. The accelerometer is configured to measure movement of the head of the user (e.g., during a seizure or other involuntary movement) during an EEG measurement and transmit signals describing measured movement to the controller.

Therefore, by connecting the controller 102 to the headset 101 via an electrode body 120 located at the side of the head of the user (e.g., T3, T4) the system 100 enables the user to lie down on their back or their side (opposite the connection to the controller) without trapping the external connection cord between the user and the surface of the bed and causing discomfort. Thereby the user can participate in an extended EEG test, such as a sleep study, with a greater level of comfort.

3.8 Electrode Housing Position

In one implementation, the EEG headset includes a set of electrodes connected via a set of spring elements 104 and arranged in the international 10-20 pattern. A first subset of (e.g., two) electrode bodies can include five spring receivers (e.g., at 0°, 45°, 90°, 135°, and 180°. positions) and a strap connector (e.g., at 270° position) and can be configured to locate at T3 and T4 locations. A second subset of (e.g., three) electrode bodies can include four spring receivers (e.g., at 0°, 90°, 180°, and 270° positions) and can be configured to locate at Fz, Cz, and Pz locations. A third subset of (e.g., two) electrode bodies can include three spring receivers (e.g., at 0°, 90°, and 180°. positions) and can be configured to locate at FpZ and Oz locations. A fourth subset of (e.g., fourteen) electrode bodies can include two spring receivers (e.g., at 0° and 180°. positions) and can be configured to locate at Fp1, F7, T5, O1, O2, T6, F8, Fp2, F3, F4, C3, C4, P3, P4, locations. At position T3, a 5-position electrode body 120 can be connected to 4 spring elements, one chin strap, and an external connection cable. At position T4, a 5-position electrode body 120 can be connected to 4 spring elements and one chin strap. At positions Fz, Cz, and Pz, a 4-position electrode body 120 can be connected to adjacent electrodes via a spring element 110 arranged along a medial and lateral plane. In this implementation, at positions Fp1, F7, T5, O1, O2, T6, F8, and Fp2, a 2-position electrode body 120 can be connected to adjacent electrodes via a spring element 110 along a circumferential path. At positions F3, F4, C3, C4, P3, and P4, a 2-position electrode body 120 can be connected to adjacent electrodes via a spring element 110 along a lateral path. At position Fpz, a 3-position photosensor housing 121 can be connected to adjacent electrodes along the medial plane and the circumferential path. In one variation, the housing 121 located at Fpz is a 2-position photosensor housing 121 connected to adjacent electrodes along a circumferential path. In another variation, the housing 121 located at Fpz is a bridge housing 121. In another variation, the housing 121 located at Fpz is an electrode body 120. At position Oz, a 3-position bridge housing 121 can be connected to adjacent electrodes along the medial plane and the circumferential path. In one variation, the housing 121 located at Oz is a 2-position bridge housing 121 connected to adjacent electrodes along a circumferential path. In one variation, a 2-position electrode body 120 can be connected to adjacent electrodes via a spring element 110 arranged along a lateral plane at positions Fz, Cz, and Pz. In another variation, the housing 121 located at Oz is an electrode body 120.

However, the EEG headset can include a set of electrodes connected via a set of spring elements 104 and arranged a pattern other than the international 10-20 standard pattern or include additional housings 121 (and necessary spring elements to support) in other locations on the head.

3.6 Additional Housing Configurations

As described above, each electrode body 120 can include a base configured for assembly within a singular electrode position or within a small subset of electrode positions. Therefore, the system can include groups of unique electrode bodies 120.

Conversely, a first electrode body 120 of the system can include a base identical to the base of a second electrode body 120 and can include receiving element positions configured to receive and retain all permutations of spring elements, chin strap receivers, and external cable combinations to form a complete 10-20 EEG headset. For example, each electrode body 120 can include a set of receiving elements positioned in a radially-symmetrical pattern at 0°, 45°, 90°, 135°, 180°, 225°, 270°, and 315° positions. In this example, a system can further include a set of inserts configured to locate within and enclose unused receiving elements within electrode bodies of the headset, such as to prevent hair entanglement within these unused receiving elements.

In one implementation, the electrode body 120 can be configured to orient spring elements at an oblique angle to the housing 121 to accommodate the curvature of the head of the user. For example, an electrode body 120 can define a housing 121 including a spring element receiver 126 arranged at a circumferential surface 125 of the housing 121 and configured to connect a spring element 110 to the housing 121 at an oblique angle. In one variation, the oblique orientation of the spring element receiver 126 cooperates with the angle of an arcuate section of the spring element 110 to create an angle between the spring element no and the housing 121 that best matches the curvature of the head of a multitude of users, thereby producing a headset 101 that is more comfortable for the multitude of users.

4. Spring Elements

Generally, the system includes a set of spring elements 104 configured to: mechanically couple adjacent electrodes; to expand and contract to accommodate different head sizes and shapes; and to locate adjacent electrodes in relative positions that approximate an EEG standard (e.g., the 10-20 system).

In one implementation, a spring element 110 is arranged in a serpentine shape to construct a flat spring. In particular, the spring element 110 is arranged in a boustrophedonic pattern, with the spring element no extending in a first direction, curving 90°, and extending a distance in a second direction perpendicular to the first direction, subsequently curving 180° and extending in a third direction parallel and opposite the second direction, subsequently curving 180° and extending in the second direction, subsequently curving 90° and extending in the first direction. Furthermore, adjacent and nominally-parallel sections of the spring element no are offset and each return end of a spring element no, characterized by a large and smooth curve, maintains a gap between the adjacent section and the return end to reduce or eliminate pinch points that may catch or pull on a user's hair while wearing the headset.

4.1 Linear Extension

In one implementation, the system 100 includes: a first spring element 110 defining a first spine 111 exhibiting a first spring rate; and a second spring element 110 defining a second spine 11 exhibiting a second spring rate, different from the first spring rate. The first spring element 110 cooperates with the second spring element 110 to constrain the spacing of the set of electrode bodies 105 to repeatably locate the set of electrode bodies 105 at a set of positions on a head of a user for a range of head sizes.

In one example, a first spring element 110 of a first spring rate is arranged between a first electrode body 120 located at the T3 electrode position and a second electrode body 120 located at the C3 electrode position, and a second spring element 11o of a second spring rate is arranged between the first electrode body 120 and a third electrode body 120 located at the T5 electrode position. The first distance between the T3 electrode position and the C3 electrode position is greater than the second distance between the T3 electrode position and the T5 electrode position. Therefore, the first spring element 110 is required to extend a greater distance than the second spring element 110. The lower spring rate of the first spring element no enables greater variation in position between the electrode body 120 located at the T3 electrode position and the electrode body 120 located at the C3 electrode position, compared to the electrode body 120 located at the T3 electrode position and the electrode body 120 located at the T5 electrode position.

In another implementation, a first spring element no includes a cross-section of a first thickness, and a second spring element no includes a cross-section of a second thickness less than the first thickness. Accordingly, the second spring element 110 exhibits a lower spring rate than the first spring element 110.

In another implementation, a first spring element no includes a first number of turns and a second spring element 110 includes a second number of turns less than the first number of turns. Accordingly, the second spring element no extends less than the first spring element no when a tension force is applied to the spring element no, and the second spring element no exhibits a lower spring rate than the first spring element no.

In another implementation, a first spring element no includes a first return radius, and a second spring element no includes a second return radius less than the first return radius. Accordingly, the second spring element no exhibits a higher spring rate than the first spring element no.

In another implementation, a first spring element no includes a first length between turns, and a second spring element no includes a second length between turns that is less than the first length between turns. Accordingly, the second spring element no extends less than the first spring element no when a tension force is applied to the spring element no (e.g., exhibits a lower spring rate.)

In another implementation, a spring element no can incorporate a cross section with a varying thickness or varying return radii in order to produce different spring rates as a function of travel, to construct a spring element no with a non-uniform flex pattern.

4.2 Angular Flexion

Figure 3A:
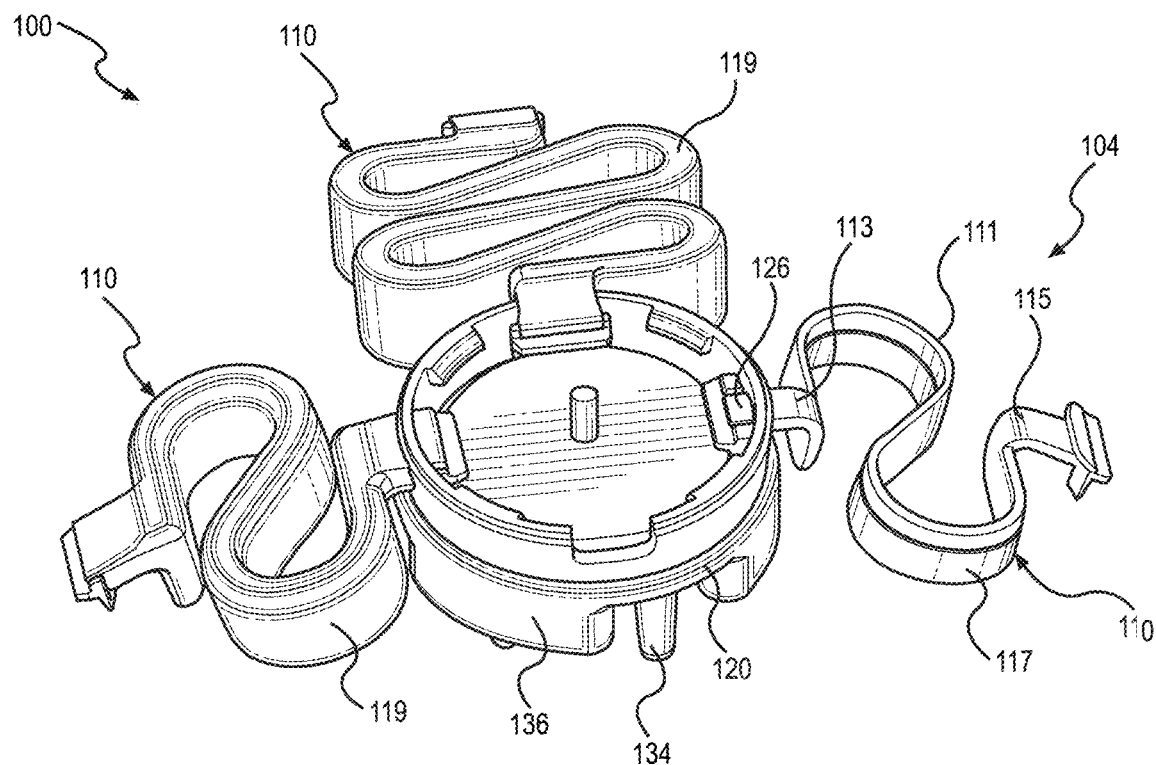
FIGS. 3A-3B are schematic diagrams of one variation of the system.
Figure 3B:
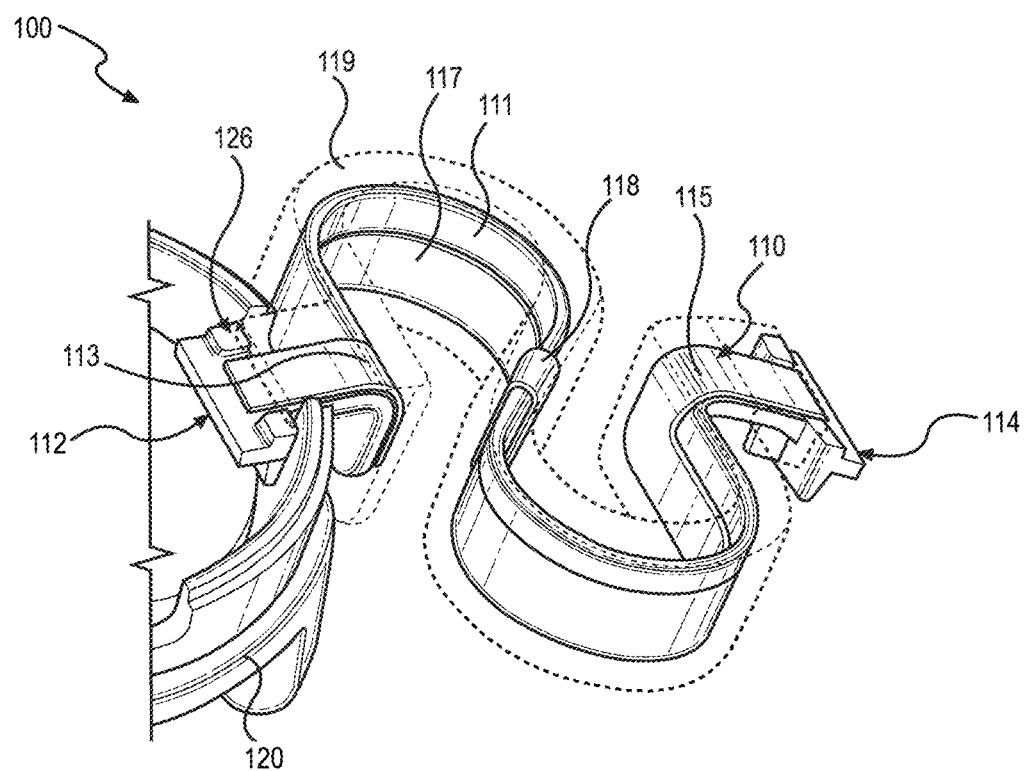

In another implementation as shown in FIGS. 3A-3B, the spring element 110 is configured with a first arcuate section 113, located at the proximal end 112, of a first elasticity, and a second arcuate section 115, located at the distal end 114, of a second elasticity. The first arcuate section 113 and the second arcuate section 115 enable the spring element 110 to flex in a second degree of freedom (e.g., angular flexion) in addition to the first degree of freedom (e.g., longitudinal extension via the serpentine geometry of the center section). The angular flexion of the spring element 110 enables the headset 101 to conform more closely to the curvature of a user's head, increasing comfort for the user, especially during periods of extended wear (e.g., sleep study).

For example, a first spring element 110 with a first arcuate section 113 of a first elasticity and a second arcuate section 115 of the first elasticity, is arranged between a first electrode body 120 located at the C3 electrode position and a second electrode body 120 located at the Cz electrode position, and a second spring element 110 of a first arcuate section 113 of a second elasticity and a second arcuate section 115 of the second elasticity, is arranged between the first electrode body 120 and a third electrode body 120 located at the T3 electrode position. The first curvature of the head of the user between the C3 electrode position and the Cz electrode position is greater than the second curvature of the head of the user between the C3 electrode position and the T3 electrode position, therefore the first arcuate section 113 and the second arcuate section 115 of the first spring element 110 are required to flex a greater distance than the first arcuate section 113 and the second arcuate section 115 of the second spring element 110.

In one implementation, the set of spring elements 104 includes a first spring element 110 including a first arcuate section 113 of a first elasticity; and a second arcuate section 115 of a second elasticity, greater than the first elasticity. The first spring element 110 is configured to mechanically couple to a first electrode body 120 proximal the first arcuate section 113; locate the first electrode body 120 proximal a first location on the head of a user exhibiting a first curvature; couple to a second electrode body 120 proximal the second arcuate section 115; and locate the second electrode body 120 proximal a second location on the head of a user exhibiting a second curvature, greater than the first curvature.

For example, a spring element no includes a proximal end 112 defining a first arcuate section 113 of a first elasticity and a distal end 114 defining a second arcuate section 115 of a second elasticity, greater than the first elasticity, is arranged between a first electrode body 120 located at the T3 electrode position and a second electrode body 120 located at the C3 electrode position. The curvature of the head of the user proximal the C3 electrode position is greater than the curvature of the head of the user proximal the C3 electrode position. The spring element no is coupled to the first electrode body 120 at T3 via the proximal end 112 and is coupled to the electrode body 120 at C3 via the distal end 114. The spring element no exhibits angular flexion at the second arcuate section 115 greater than the angular flexion exhibited at the first arcuate section 113, based on the curvature of the head of the user. Therefore, the spring element no can include a first arcuate section 113 and a second arcuate section 115 configured to flex independently to different angles of flexion to conform to the curvature of the head of the user.

In another variation, the system 100 includes a set of spring elements 104 including a first spring element no including: a first spring element defining a first proximal arcuate section bending by a first angular amplitude, and a first distal arcuate section, bending by the first angular amplitude; and a second spring element defining a second proximal arcuate section bending by a second angular amplitude, and a second distal arcuate section, bending by the second angular amplitude. The first spring element cooperates with the second spring element to constrain the angular flexion of a set of electrodes to repeatably locate the set of electrodes at a set of positions on a head of a user for a range of head shapes (e.g., whole head curvature, local curvature).

In one example in which a local region of the head of the user exhibits a low curvature (e.g., is flatter), the electrode bodies 120 located at the Cz, and Pz electrode locations in the 10-20 system line are colinear, and the electrode body 120 at Pz is oblique to the electrode body at Cz. The spring element 100 includes a proximal end 112 with a first arcuate section 113 defining a bend of 90 degrees between the serpentine geometry of the center section 116, and the electrode body 120 at Cz, thereby arranging the electrode body 120 at Cz and the spring element 120 colinear. The distal end 114 of the spring element 120 defines an oblique bend, and couples to the electrode body 120 at Pz to match the curvature of the head of the user.

Therefore, the first spring element no can flex a first angle at the first arcuate section 113 and a second angle at the second arcuate section 115 to accommodate the curvature of a user's head. The degree of freedom enabled by the angular flexion of the flexible arcuate sections of the spring element no can enable the headset 101 to conform to the curvature of the head of a user more closely. Further, the elasticity of the first arcuate section 113 and the second arcuate section 115 can be configured to conform to multiple curvatures to accommodate the heads of multiple users without reconfiguring the headset 101.

In another example in which the head of the user is of a first size, the headset 101 includes: a first spring element defining a first center section extended a first linear amplitude, a proximal end including a first arcuate section bending by a first angular amplitude, and a distal end including a second arcuate end bending by a second angular amplitude; and a second spring element including a second center section extended a second linear amplitude greater than the first linear amplitude, a second proximal end including a third arcuate section bending by a third angular amplitude less than the first angular amplitude; and a second distal end including a fourth arcuate end bending by a fourth angular amplitude less than the second angular amplitude.

Therefore, the headset 101 can include the set of spring elements 104 including spring elements 110 capable of extending through a range of amplitudes that can accommodate a range of head sizes of multiple users, eliminating the need to reconfigure the headset 101 between applications to multiple users, or to customize the headset 101 for each particular user.

4.3 Spring Element Manufacturing

In one implementation, a spring element no can be formed from an injection molded polymer and can be arranged in a serpentine shape to form a flat spring. The spring element no also includes a channel that can receive a cable. In another implementation, the spring element no can be formed from metal, plastic, or a composite material. In another implementation, shown in FIGS. 3A-3B, the spring element 11o additionally includes an insulative layer 119 encasing the conductive element 117 and center section 116 of the spring element no. In one example, the insulative layer 119 is additionally water resistant. Further, the connection interface between the spring element no and the electrode body 120, as well as any other gaps in the electrode body 120, are sealed to be water resistant, thereby enabling the headset to be submerged in a liquid (e.g., soap and water, a disinfectant solution) to be cleaned without disassembly.

4.4 Cable Routing

In one implementation, the spring element no includes a hollow cross-section constructing a traversable cavity from a proximal end 112 of the spring element 110 to a distal end 114 of the spring element no opposite the proximal end 112. A cable can be disposed within the cavity. In one variation, the spring element no includes a U-shaped cross-section open to the exterior of the spring element no. For example, the open, U-shaped cross-section can enable an assembler to insert a cable into the channel for ease of assembly, thus reducing assembly cost. In another variation, after a cable is inserted, the spring element no and the joint between the spring element no and the electrode body 120 is hermetically sealed.

In another implementation, the spring element no defines a spine 111 and a conductive element 117 defining a flexible PCB (e.g., flexible printed circuit/FCP) mounted to one face of the spine 111. The conductive element 117 terminates at the proximal end 112 and the distal end 114 of the spring element no at an electrical coupling configured to couple the conductive element 117 to the electrical circuit 123 of an electrode body 120. For example, as shown in FIGS. 3A-3B, the spring element no includes: a center section 116 defining a spine 111; and a conductive element 117 defining a flexible printed circuit board coupled to and extending along the spine 111 between the proximal end 112 and the distal end 114.

In another implementation, a conductive element 117 defining a flexible PCB is mounted to one face of the spine 111 of a center section 116 defining a two-loop serpentine. The flexible PCB is mounted to a first face of the spine 111, and is connected to a first electrical coupling at the proximal end 112. Due to the geometry of the two-loop serpentine, the flexible PCB transitions to a second face of the spine, opposite the first face, to connect to a second electrical coupling at the distal end 114. The flexible PCB transitions at a conductive element transfer 118 located on the center section between the proximal end 112 and the distal end 114. The conductive element transfer 118 defines a length of flexible PCB connected to a first section of the conductive element 117 extending along the spine 111 to the proximal end 112, executing a 90 degree turn toward an edge of the spine 111, curling over the edge of the spine to the second face, opposite the first face, executing a second 90 degree turn toward the length of the spine 111, and connected to a second section of the conductive element 117 extending along the spine to the distal end 114.

In one example, shown in FIG. 3B, the spring element no includes: a center section including a first spine defining a two-loop serpentine; and a first conductive element defining a proximal connector extending from the proximal end of the first spine and configured to electrically couple to a first electrical circuit, a proximal section coupled to a first face of the spine and extending from the proximal connector along a first face of the spine, a conductive element transfer extending between the proximal section over an edge of the spine between the first face of the spine and a second face of the spine, a distal section coupled to the second face of the spine and extending from the conductive element transfer along the second face of the spine, and a distal connector coupled to the distal section and extending from the distal end of the first spine and configured to electrically couple to a second electrical circuit. The spring element no can further include an insulative layer encasing the conductive element and the spine. Additionally, the spring element 110 including a center section 116 with an even number of turns (e.g., 2, 4, 8, 12) includes a conductive element transfer 118.

In another implementation, the spring element 110 includes a center section 116 including a spine 111 defining a three-loop serpentine. The conductive element 11 is arranged on a first face of the spine and extends between the proximal end and the distal end. The spring element 110 can further include an insulative layer encasing the conductive element and the spine. Due to the geometry of the three-loop serpentine, the conductive element transfer 118 is not required for the conductive element 117 to connect with the proximal electrical connector and the distal electrical connector. Additionally, a spring element no including a center section with an odd number of turns (e.g., 1, 3, 7, 11) includes the conductive element 117 mounted to only one face of the spine 111.

4.5 Spring Element Distribution and Tuning

Generally, the system can include a set of springs configured to connect adjacent electrodes and characterized by spring rates inversely proportional to variances in the distances between adjacent electrodes necessary to achieve the electrode standard (e.g., 10-20 EEG standard) across a population of users with different head sizes and shapes. In particular, in the international 10-20 system, the electrode at position F3 can vary more than the electrode at position T5. A spring element no with a first spring rate can connect the electrode at position F3 to the electrodes at positions T3 and Fz, and a spring element no with a second spring rate greater than the first spring rate can connect the electrode at position T5 to electrodes at positions T3 and O1. Generally, an electrode located at a medial position (e.g., Fpz, Fz, Cz, Pz, and Oz) will remain on the medial plane as the headset flexes, and the spring elements connected to either side of the electrode in the lateral direction can flex equally in both directions.

In one example, the system 100 includes a first spring element no including a first spine 111 exhibiting a first spring rate corresponding to a first electrode spacing ratio of 10 percent of the distance across the surface of a head of a user between a first landmark and a second landmark, and a second spring element 110 including a second spine 111 exhibiting a second spring rate corresponding to a second electrode spacing ratio of 20 percent of the distance across the surface of a head of a user between the first landmark and the second landmark.

In one implementation, the EEG headset includes a set of electrode bodies connected by spring elements in a chain pattern. A chain pattern of electrode body 120 and spring element 110 connections is defined as: a proximal end 112 of a first spring element 110 connected to a first electrode body 120, the distal end 114 of the first spring element 110 connected to a second electrode body 120, a proximal end 112 of a second spring element no connected to the second electrode body 120 opposite the first spring element no, and a distal end 114 of the second spring element no connected to a third electrode body 120, etcetera. A first set of spring elements 104 with a first spring rate can connect electrode bodies in the chain pattern as described above along a circumferential path around the user's head with the following connections: Fpz connected to Fp1, Fp1 connected to F7, F7 connected to T3, T3 connected to T5, T5 connected to O1, O1 connected to Oz, Oz connected to O2, O2 connected to T6, T6 connected to T4, T4 connected to F8, F8 connected to Fp2, and Fp2 connected to Fpz. A second set of spring elements 104 with a second spring rate less than the first spring rate can connect the electrodes along a medial path in the following pattern: Fpz connected to Fz, Fz connected to Cz, Cz connected to Pz, and Pz connected to Oz. A third set of spring elements 104 with the second spring rate can connect the electrodes along a lateral path in the following pattern: T3 connected to F3, F3 is connected to Fz, Fz connected to F4, and F4 connected to T4. A fourth set of spring elements 104 with the second spring rate can connect the electrodes along a lateral path in the following pattern: T3 connected to C3, C3 connected to Cz, Cz connected to C4, and C4 connected to T4. A fifth set of spring elements 104 with the second spring rate can connect the electrodes along a lateral path in the following pattern: T3 connected to P3, P3 connected to Pz, Pz connected to P4, and P4 connected to T4. In one variation, the medial electrodes Fpz, Fz, Cz, Pz, and Oz are connected to adjacent electrodes along lateral paths only (e.g., Fp1, Fp2; F3, F4) In another variation, a set of spring elements 104 of another spring rate are used in the same connection patterns.

In another variation, a kit of spring elements includes a set of spring elements 104 of various spring rates and is included with the EEG headset. An operator can assemble electrode bodies and spring elements into a customized EEG headset unique to the user. However, the system can include a set of springs and electrode bodies configured in any pattern to connect the electrodes to maintain electrode position in the 10-20 EEG standard.

5.1 Additional Support Member

In one implementation, the system can include an elastic support member proximal to the circumference of the EEG headset maintain electrode position in the 10-20 EEG standard and arrest movement of the headset in relation to the user's scalp if the user moves. For example, the elastic support member can be attached to an electrode body 120 at Fpz, passed around the circumference of a user's head and attached to an electrode body 120 at Oz, and then passed around the opposite side of the user's head and attached to Fpz. In another variation, the elastic member can be attached to a set of electrodes at Fpz (or an adjacent electrode position) and subsequently attached to a set of electrodes at Oz (or an adjacent electrode position).

6. Controller

In one implementation, the EEG headset includes a controller 102 connected to an external connection housing 121 via the external connection cable, the controller 102 including: an electrical circuit, a processor, storage, memory, and an external device connection. The controller 102 can be configured to receive electrical signals from the set of electrodes, process the electrical signals to produce an output, and transmit the output to an output device (e.g., a monitor or a computer) to further process, analyze, or display the output.

In another example, a headset 101 worn by a user during a test can be connected to the controller 102. The controller 102 can be connected to a monitor displaying the data output. As the test progresses, the electrodes can produce electrical signals that are transmitted to the controller 102. The controller 102 then processes these electrical signals into an output readable by the monitor. The controller 102 then transmits the output to the monitor, and the monitor displays the data output to a technician conducting the test. Therefore, the controller 102 houses the electrical components not required proximal the electrode for the electrode to function, (e.g., signal processing, power) at a location other than the user's head, resulting in an EEG headset that is comfortable to wear for an extended period. In one variation, the controller 102 is miniaturized, lightweight, and is arranged within one of the bridge housings.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:
1. An electroencephalography headset comprising:
a set of electrodes configured to detect electroencephalographic signals from a head of a user; and
a set of spring elements:
  interconnecting and configured to elastically locate the set of electrodes on the head of the user;
  configured to elastically deform to accommodate a size of the head of the user; and
  comprising a first spring element:
    coupling a first electrode in the set of electrodes to a second electrode in the set of electrodes;
    comprising:
      a first spine comprising:
        a first spring segment; and
        a second spring segment cooperating with the first spring segment to define a first serpentine geometry comprising an even quantity of loops;
      a first flexible circuit board comprising:
        a first circuit board segment arranged along a first side of the first spring segment; and
        a second circuit board segment arranged along a second side of the second spring segment; and
        a conductive transfer element:
          interposed between the first circuit board segment and the second circuit board segment;
          extending over an edge of the first spine; and
          extending between the first side of the first spring segment and the second side of the second spring segment; and
    configured to maintain relative positions of the first electrode and the second electrode according to an electroencephalography standard.

2. The electroencephalography headset of claim 1, further comprising a first electrode tip:
  configured to transiently locate onto and electrically couple to an electrode interface of the first electrode; and
  comprising:
    a conductive probe configured to electrically couple to the head of the user; and
    an insulative boss configured to contact the head of the user and transfer a weight of the electroencephalography headset into the head of the user.

3. The electroencephalography headset of claim 2, wherein the first electrode further comprises an electromagnetic shield:
  comprising a conductive injection-molded polymer;
  extending toward the conductive probe; and
  configured to shield the conductive probe from external electromagnetic radiation.

4. The electroencephalography headset of claim 1, further comprising:
  a set of electrode tips, each electrode tip in the set of electrode tips:
    electrically coupled to an electrode in the set of electrodes; and
    comprising:
      an electrode base:
        comprising a conductive material;
        configured to transiently install on an electrode body housing the electrode; and
        configured to electrically couple to an electrode interface of the first electrode;
      an elastic beam comprising the conductive material and extending from the electrode base;
      a conductive probe:
        arranged on a distal end of the elastic beam opposite the electrode base;
        defining a first contact area configured to contact and electrically couple to the head of the user; and
        configured to conduct electrical signals from the head of the user into the electrode interface via the elastic beam and the electrode base; and
      a boss:
        comprising an insulative material;
        extending from the electrode base opposite the electrode interface; and
        defining a second contact area greater than the first contact area, the second contact area configured to:
          contact the head of the user; and
          and carry a weight of the electroencephalography headset to the head of the user.

5. The electroencephalography headset of claim 1:
  wherein the first spring element further comprises a first water-resistant insulative layer encasing the first flexible circuit board; and
  wherein the first spine comprises a non-conductive injection-molded polymer forming a first flat spring defining the first serpentine geometry.

6. The electroencephalography headset of claim 1:
  wherein the first flexible circuit board is adhered along a first side of the first spine; and
  wherein the first flexible circuit board and the first spine are coated with an insulative layer.

7. The electroencephalography headset of claim 1:
  wherein the first spring element comprises a first non-conductive injection-molded polymer characterized by a first elasticity; and
  further comprising a second spring element:
    coupling the first electrode to a third electrode in the set of electrodes;
    comprising a second spine defining the first serpentine geometry;
    comprising a second non-conductive injection-molded polymer characterized by a second elasticity different from the first elasticity; and
    characterized by a second spring rate different from a first spring rate.

8. The electroencephalography headset of claim 1, wherein the first electrode comprises a unitary structure comprising:
  an electrode body comprising an insulative polymer housing;
  an electrode interface comprising a conductive polymer; and
  an electromagnetic shield:
    comprising a conductive polymer;
    extending from the electrode interface toward the head of the user, radially offset from and encircling a boss; and
    configured to shield a conductive probe from external electromagnetic radiation.

9. The electroencephalography headset of claim 1:
  wherein the first electrode comprises an electrode tip configured to contact the head of the user at a first reference location proximal a first ear of the user; and wherein the second electrode comprises:
  an electrode tip configured to contact the head of the user at a second reference location proximal the first ear of the user and offset from the first reference location by a first distance; and
  an accelerometer configured to measure movement of the head of the user.

10. The electroencephalography headset of claim 1, wherein the first electrode comprises:
  a housing comprising a first magnetic element; and
  a first electrode tip:
    comprising a second magnetic element configured to transiently couple to the first magnetic element to retain the electrode tip on the housing; and
    configured to rotate about an axis of the housing coaxial with the first magnetic element.

11. The electroencephalography headset of claim 1, further comprising a second spring element:
  coupling the first electrode to a third electrode in the set of electrodes;
  comprising:
    a second spine comprising:
      a third spring segment; and
      a fourth spring segment cooperating with the third spring segment to define a second serpentine geometry comprising an odd quantity of loops;
    a second flexible circuit board comprising:
      a third circuit board segment arranged along a first side of the third spring segment; and
      a fourth circuit board segment arranged along a second side of the fourth spring segment; and
  cooperating with the first spring element to maintain relative positions of the first electrode, the second electrode, and the third electrode according to the electroencephalography standard.

12. The electroencephalography headset of claim 11:
  wherein the first spring element is characterized by:
    a first cross-sectional area; and
    a first spring rate; and
  wherein the second spring element is characterized by:
    a second cross-sectional area greater than the first cross-sectional area of the first spring element; and
    a second spring rate greater than the first spring rate.

13. The electroencephalography headset of claim 11, wherein the first spring element and the second spring element cooperate to maintain relative offsets between of the first electrode, the second electrode, and the third electrode according to a 10-20 electroencephalography standard.

* * * * *